United States Patent [19]

Barker et al.

[11] Patent Number: 4,663,449

[45] Date of Patent: May 5, 1987

[54] PROCESS FOR EFFECTING ALDOSE TO KETOSE CONVERSION

[75] Inventors: Sidney A. Barker; Peter J. Somers, both of Birmingham, England

[73] Assignee: Imperial Chemical Industries PLC, London, England

[21] Appl. No.: 551,694

[22] Filed: Nov. 14, 1983

[30] Foreign Application Priority Data

Nov. 16, 1982 [GB] United Kingdom ............... 8232725
Sep. 30, 1983 [GB] United Kingdom ............... 8326265

[51] Int. Cl.$^4$ .............................................. C07H 1/00
[52] U.S. Cl. .................................... 536/125; 536/1.1; 536/124
[58] Field of Search ................................ 536/1.1, 125

[56] References Cited

U.S. PATENT DOCUMENTS 3,256,270 6/1966 Haack et al. ..................... 536/125
3,431,253 3/1969 Parris ................................ 536/125
3,850,905 11/1974 Tumerman et al. ............. 536/125
3,875,140 4/1975 Barker et al. ..................... 536/125

OTHER PUBLICATIONS

Ozaki et al., "Chem. Abst.", vol. 80, 1974, p122656(r).
DeWit et al., "Carbohydrate Research", vol. 74, 1979, p. 157.

Primary Examiner—Johnnie R. Brown
Attorney, Agent, or Firm—Cushman, Darby & Cushman

[57] ABSTRACT

A process for the conversion of an aldose, or a substituted aldose, to a ketose, or a substituted ketose, in an aqueous reaction mixture containing a halide of a metal from Group II of the Periodic Table at a concentration in the range 0.5 molar to saturation. The process is particularly suitable for converting glucose into fructose. The preferred metal halide is calcium chloride.

10 Claims, No Drawings

PROCESS FOR EFFECTING ALDOSE TO KETOSE CONVERSION

This invention relates to a process for effecting aldose to ketose conversion and in particular to a process for converting glucose to fructose or a mixture containing glucose and fructose or to a process for increasing the proportion of fructose in a mixture containing glucose and fructose.

Fructose is sweeter than its naturally-occurring isomer glucose and in consequence high-fructose syrups have advantages for use as sweeteners in products such as confectionary and cakes. During the past twenty years there has been considerable research into processes for producing high fructose syrups for such uses. Processes available for converting glucose to fructose or fructose-containing syrups can be enzymatic, using the enzyme glucose isomerase, or chemical. Enzymatic processes are usually preferred since chemical processes tend to produce complex mixtures of sugars comprising mannose and there is a tendency for fructose produced during chemical processes to revert to glucose or mannose under the conditions employed in the process. Chemical isomerisations of aldoses or ketoses under alkaline conditions, using for example calcium hydroxide have been extensively studied. In this and similar isomerization reactions an equilibrium is established between the ketose and the related C-2 epimeric aldoses, for example between fructose and glucose and mannose. It is a particular feature of these isomerisations that they are reversible so that for example the fructose produced by isomerisation of glucose and/or mannose can be converted back to glucose and mannose. $CaCl_2$ (0.1M) has been used in an alkaline isomerisation of glucose and/or mannose to fructose with 0.25M KOH (G. De Wit, A. P. G. Kieboom and H. Van Bekkum, Carbohyd. Res., 74 (1979) 157). In this work $CaCl_2$ was shown to enhance the formation of a UV absorbing material attributed to an enediol-anion species.

According to the present invention we provide a process for effecting conversion of an aldose, or a substituted aldose, to a ketose, or a substituted ketose, which comprises a step wherein a reaction mixture is formed comprising an aldose or substituted aldose, water and a halide of a metal from Group II of the Periodic Table, preferably a chloride, the metal halide being present in the reaction mixture in a concentration within the range 0.5 molar to saturation.

The metal halide may be introduced into the reaction mixture either as the halide per se or as a precursor which forms the halide under the conditions prevailing in the reaction. It may be introduced in the form of a complex with the aldose or substituted aldose.

A feature of the process of the invention is its specificity. By this process an aldose is essentially converted solely to the corresponding ketose with essentially no concomitant production of the C-2 epimer. Additionally there is essentially no tendency for the produced ketose to revert to the aldose from which it is derived.

The process of the invention is generally applicable to the conversion of aldoses into ketoses or of substituted aldoses into substituted ketoses. It may be applied to the conversion of an aldose into a ketose or into an aldose-ketose mixture. Alternatively it may be used to convert an aldose-containing mixture of sugars into a mixture containing a ketose or an aldose and a ketose. It is also very suitable for converting a sugar mixture comprising an aldose and a ketose into a mixture containing an increased proportion of a ketose. Preferably the aldose is D-glucose or L-glucose and the corresponding ketose is D-fructose or L-fructose respectively. The process of the invention is very usefully applied to effect conversion of a mixture comprising glucose and fructose into one containing an increased proportion of fructose. The aldose or aldose-containing mixture may have been produced and be supplied directly from another process, for example a process for the solubilisation and/or hydrolysis of cellulose such as that described in our published European Patent Specification No. 44622.

Other conversions of aldoses to ketoses or of substituted aldoses to substituted ketoses which may usefully be effected by the process of the present invention include xylose to xylulose, lactose to lactulose and the following:

D-mannose→D-fructose
L-mannose→L-fructose
D-galactose→D-tagatose
D-talose→D-tagatose
6-Deoxy-L-mannose→6-deoxy-L-arabino-hexulose
6-Deoxy-D-glucose→6-deoxy-D-arabino-hexulose
  (otherwise 6-deoxy-D-fructose)

For a variety of reasons including general convenience the preferred halide for use in the process is calcium chloride. Other suitable but less preferred metal halides are the chlorides or bromide of magnesium and zinc and calcium bromide. The preferred halide calcium chloride is available in anhydrous form or in a number of hydrated forms including the monohydrate $CaCl_2 \cdot H_2O$; the dihydrate $CaCl_2 \cdot 2H_2O$, the tetrahydrate $CaCl_2 \cdot 4H_2O$ and the hexahydrate $CaCl_2 \cdot 6H_2O$. The manner in which it is included in the reaction mixture depends upon which form is used.

Suitably the conversion of the aldose or substituted aldose to the corresponding ketose or substituted ketose is effected in a reaction mixture the pH of which is on the acid side of neutrality. Preferably the pH of the reaction mixture when calcium or magnesium halides are used is within the range 2 to 7 and especially within the range 3 to 6.5. When zinc halides are used lower pHs are preferred. The pH of the reaction mixture may be controlled by any suitable means. Suitable means include addition of calcium carbonate, calcium hydroxide or other suitable bases either initially or during the course of the conversion. The pH may also be controlled by additions of the anhydrous chloride of a Group II metal, particularly calcium chloride, during the reaction and by suitable variations of the source of the calcium or other Group II metal chloride and of the sugar content of the reaction mixture.

A suitable temperature for the contacting step is in the range 20° to 100° C., temperatures in the range 30° to 85° C. being preferred. Suitable periods are dependent on other reaction parameters such as temperature, concentrations of reagents, and pH. Lower temperatures for instance require longer reaction times. Preferably the reaction should be performed with the exclusion of oxygen.

After the reaction, the metal and/or halide ions in the resulting product may be separated by any suitable method and separated ions may be returned to the reaction step by suitable means as part of a continuous process. The ketose-containing syrup produced by the process may, after separation of metal and/or halide ions, be used as it is even if it contains a mixture of sugars or, if it is a mixture, it may be treated to separate individual sugar components. Where an aldose-ketose mixture is produced and the components are separated, the aldose component may be returned to the reaction step for further treatment.

It is an advantage of the process of the invention that, when it is used to convert glucose into fructose or into high fructose syrups, significant amounts of mannose are not obtained. This is most unusual for a chemical process for converting glucose to fructose.

It is also possible by the process of the invention to achieve simultaneous conversion of two C-2 epimerically related aldoses to the same ketose. Thus glucose and mannose in admixture can be converted to fructose. An example of this effect would be the exploitation of the known occurrence of a β-glucan and a mannan in yeast cells (*Saccharamyces cerevisiaie*) initially by using $CaCl_2/HCl$ for selective extraction/hydrolysis and after removing HCl, the calcium chloride used alone to produce fructose. It has also been shown that two other C-2 epimerically related aldoses, galactose and talose can be converted into the same ketose tagatose.

The invention is illustrated by the following Examples:

EXAMPLE 1

D-glucose was contacted with aqueous calcium chloride by dissolving D-glucose (to a final concentration of 1% w/w) in melted $CaCl_2:6H_2O$. The correct concentration of calcium chloride in the reaction mixture was achieved by adding anhydrous $CaCl_2$ to a final concentration of 12.5% w/v in the total mixture. Dissolution was affected at 50° C. After maintaining the mixture for one hour at 50° C. an aliquot (0.5 cm$^3$) was removed and was diluted to 10 cm$^3$ with distilled water. This diluted aliquot was analysed by conventional anion exchange chromatography of borate complexes for carbohydrate composition. It showed the presence of glucose (78%) and of fructose (22%).

EXAMPLE 2

A series of solutions was prepared containing the following amounts of anhydrous $CaCl_2$ and water:

| Solution | A | B | C | D | E |
|---|---|---|---|---|---|
| $H_2O$ | 9.0 g | 8.0 g | 7.0 g | 6.0 g | 5.0 g |
| $CaCl_2$ | 1.0 g | 2.0 g | 3.0 g | 4.0 g | 5.0 g |

To each of these solutions was added D-glucose (0.25 g) and the resulting solution was maintained at 60° for 30 minutes. At the end of this period the solutions were diluted and analysed for D-glucose and D-fructose.

| Solution | A | B | C | D | E |
|---|---|---|---|---|---|
| % D-glucose | 97 | 90 | 85 | 64 | 68 |
| % D-fructose | 2 | 10 | 14 | 31 | 26 |

EXAMPLE 3

D-glucose was dissolved in melted $CaCl_2:6H_2O$ at 50° C. to give solutions of 1, 5 and 10% w/v with respect to glucose and anhydrous $CaCl_2$ was added to a final level of 12.5% w/v. After one hour at 50° C. aliquots (0.5 cm$^3$) were removed, diluted to 10 cm$^3$ and analysed for carbohydrate composition as in Example 1.

The carbohydrate compositions observed were as shown in Table 1.

TABLE 1

| Initial glucose concentration % w/v | Final composition % glucose | Final composition % fructose |
|---|---|---|
| 1 | 78 | 22 |
| 5 | 83 | 17 |
| 10 | 77 | 23 |

EXAMPLE 4

Samples were prepared by dissolving portions (0.10 g) of the appropriate carbohydrate in melted $CaCl_2:6H_2O$ (7.5 cm$^3$) in which anhydrous $CaCl_2$ (1.25 g) had been dissolved. The solutions were maintained at 50° C. for 60 minutes with stirring and were diluted to 10 cm$^3$ with melted $CaCl_2:6H_2O$. Aliquots (0.5 cm$^3$) were taken and were analyzed for carbohydrate composition as in Example 1. The product compositions observed are set out in Table 2.

TABLE 2

| Initial Carbohydrate | Product % | |
|---|---|---|
| glucose | glucose (75): | fructose (25) |
| xylose | xylose (81): | xylulose (16) |
| lactose | lactose (88): | lactulose (6) |

EXAMPLE 5

D-mannose (0.25 g) was dissolved in a solution of $CaBr_2 2H_2O$ (6 g) in water (4 g), the pH of which had been adjusted to 4.0 (with respect to separate calomel and glass electrodes at 40° C.) by addition of NaOH. The reaction vessel was then maintained at 70° for 60 minutes. After cooling the reaction mixture was analysed by borate anion exchange chromatography and shown to contain 95% fructose and 5% mannose.

EXAMPLE 6

D-mannose (0.25 g) was dissolved in a solution of anhydrous $MgCl_2$ (4 g) in water (6 g). The reaction mixture was heated at 70° C. for 60 minutes. After cooling the reaction mixture was analysed after suitable dilution and shown to contain 75% mannose and 25% fructose.

In a similar manner D-mannose (0.25 g) was reacted with a solution of anhydrous $ZnCl_2$ (8.0 g) in water (2.0 g). The reaction mixture was analysed, after 60 minutes at 70° C., and shown to contain 59% mannose and 41% fructose.

EXAMPLE 7

A solution of calcium chloride was prepared by melting calcium chloride hexahydrate and adding calcium chloride anhydrous (1.25 g to 10 cm$^3$). This mixture was heated at 50° C. until all the calcium chloride had dissolved. L-glucose (0.1 g) was added to this solution and the temperature was maintained at 50° C. for a period of 1 hour. At the end of this time the solution was diluted (1.0 cm$^3$ to 10 cm$^3$) and analysed by anion exchange chromatography of borate complexes for carbohydrate composition. It showed the presence of glucose and fructose (84% and 16% respectively).

EXAMPLE 8

D-Glucose (20 g) was dissolved in water (41.65 g) and anhydrous $CaCl_2$ (27.75 g) added. The mixture was stirred and heated at 70° C. After periods of 30, 60, 90, 120, 150 and 180 minutes further portions of anhydrous $CaCl_2$ (5.0 g) were added. After a total reaction time of 6 hours analysis showed the presence of fructose 22% and glucose 78%.

We claim:

1. A process for the conversion of an aldose to a ketose, which comprises forming an aqueous reaction mixture containing an aldose and a halide of a metal from Group II of the Periodic table, the metal halide being added to the reaction mixture wholly or in part as an anhydrous halide and being present in the reaction mixture in a concentration within the range 0.5 molar to saturation, maintaining said aqueous reaction mixture at a pH of 2 to 7 under aldose to ketose conversion conditions to convert said aldose to the corresponding ketose with essentially no concomitant production of the C-2 epimer and essentially no tendency for the produced ketose to revert to the aldose from which it is derived, and recovering a product enriched in said ketose.

2. A process according to claim 1 wherein a sugar mixture comprising an aldose and a ketose is converted to a mixture comprising an increased proportion of the ketose.

3. A process according to claim 1 wherein glucose is converted into fructose.

4. A process according to claim 3 wherein a mixture comprising glucose and fructose is converted into a mixture comprising an increased proportion of fructose.

5. A process according to claim 1 wherein the metal halide is a chloride.

6. A process according to claim 5 wherein the metal halide is calcium chloride.

7. A process according to claim 1 wherein the metal halide is selected from the group consisting of calcium and magnesium halides and the pH of the reaction mixture is in the range of 3 to 6.5.

8. A process according to claim 1 wherein the pH of the reaction mixture is controlled by the addition to the reaction mixture of an additive selected from the group consisting of calcium carbonate, calcium hydroxide and anhydrous calcium chloride.

9. A process according to claim 1 wherein the temperature of the reaction mixture is maintained at a value within the range 30° to 85° C.

10. A process according to claim 1 wherein the conversion is effected in the absence of oxygen.

* * * * *